(12) United States Patent
Isozaki et al.

(10) Patent No.: US 8,241,663 B2
(45) Date of Patent: Aug. 14, 2012

(54) LIPOSOME PREPARATION

(75) Inventors: Masashi Isozaki, Kanagawa (JP);
Keisuke Yoshino, Ann Arbor, MI (US);
Kyoko Taguchi, Kanagawa (JP);
Masayo Kondo, Kanagawa (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 452 days.

(21) Appl. No.: 10/594,427

(22) PCT Filed: Mar. 25, 2005

(86) PCT No.: PCT/JP2005/005577
§ 371 (c)(1),
(2), (4) Date: Jul. 17, 2008

(87) PCT Pub. No.: WO2005/092388
PCT Pub. Date: Oct. 6, 2005

(65) Prior Publication Data
US 2008/0279916 A1 Nov. 13, 2008

(30) Foreign Application Priority Data
Mar. 26, 2004 (JP) ................... 2004-091704

(51) Int. Cl.
*A61K 9/127* (2006.01)
*G01N 33/53* (2006.01)
(52) U.S. Cl. .................. 424/450; 977/907; 436/829
(58) Field of Classification Search .................. None
See application file for complete search history.

(56) References Cited

U.S. PATENT DOCUMENTS

| 5,192,549 | A | 3/1993 | Barenolz et al. |
| 5,213,804 | A | 5/1993 | Martin et al. |
| 5,316,771 | A | 5/1994 | Barenholz et al. |
| 5,616,341 | A * | 4/1997 | Mayer et al. .................. 424/450 |
| 5,676,971 | A * | 10/1997 | Yoshioka et al. ............. 424/450 |
| 6,562,371 | B1 | 5/2003 | Kawahara et al. |
| 2003/0129224 | A1 * | 7/2003 | Tardi et al. .................... 424/450 |

FOREIGN PATENT DOCUMENTS

| CN | 1323199 A | 11/2001 |
| EP | 1 044 679 A1 | 10/2000 |
| JP | 2-196713 | 8/1990 |
| JP | 6-501246 | 2/1994 |
| JP | 7-20857 | 3/1995 |
| JP | 2001-55343 | 2/2001 |
| KR | 96-013703 | 10/1996 |
| WO | WO 83/02069 A1 | 6/1983 |
| WO | WO 88/06442 | 9/1988 |
| WO | 92/02244 A1 | 2/1992 |
| WO | WO 00/23052 A1 | 4/2000 |
| WO | 03/015753 A1 | 2/2003 |

OTHER PUBLICATIONS

Haragai et al. Pharmaceutical Research vol. 18, No. 9 / Sep. 2001, pp. 1284-1290.*
Official Action issued in corres. CN Patent Application No. 2005800097595, Feb. 6, 2009.
English version of International Search Report dated Apr. 21, 2005.
English version of International Preliminary Report on Patentability.
Bioimaging, *Stealth Liposomes: Local Chemotherapy* (2008), http://www.bioimaging.dk/index.php?id=75, printed on Jan. 19, 2012.
Wan-Liang Lu et al., *A Pegylated Liposomal Platform: Pharmacokinetics, Pharmacodynamics, and Toxicity in Mice Using Doxorubicin as a Model Drug*, 95 J. Pharmacol Sci 381-389 (2004).
Harigai, T. et al., "Preferential Binding of Polyethylene Glycol-Coated Liposomes Containing a Novel Cationic Lipid, TRX-20, to Human Subendthelial Cells via Chondroitin Sulfate", Pharmaceutical Research, vol. 18, No. 9, pp. 1284-1290, Sep. 2001.
Office Action dated Oct. 12, 2011, issued by the Korean Patent Office in corresponding Korean Patent application No. 10-2006-7019769, with a partial English Translation.
Supplementary European Search Report issued Jun. 12, 2012 by the European Patent Office in European Patent Application No. 05721504.8.

* cited by examiner

*Primary Examiner* — Doug Schultz
(74) *Attorney, Agent, or Firm* — Buchanan Ingersoll & Rooney PC

(57) ABSTRACT

A liposome preparation is provided. This liposome preparation is capable of stably encapsulating a drug which is unstable under an acidic condition, and such stable encapsulation is realized without detracting the effect realized by the modification of the membrane by a hydrophilic macromolecule such as stability in blood. More specifically, the liposome preparation comprises a unilamellar vesicle formed from a lipid bilayer comprising a phospholipid as its main membrane component, and an interior aqueous phase of the vesicle at a pH of up to 5. The liposome has a drug loaded therein, and the vesicle is modified with a hydrophilic macromolecule only on its exterior surface.

17 Claims, 3 Drawing Sheets

LIPOSOME PREPARATION

TECHNICAL FIELD

This invention relates to a liposome preparation which is adapted for use in drug delivery system.

BACKGROUND ART

Recently, a large number of investigations have been conducted on drug delivery system (DDS) for delivering and distributing a drug to the target lesion site at high efficiency with high safety. One such approach has been use of a closed vesicle such as liposome, emulsion, lipid microsphere, or nano particle for the transporter (carrier) of the drug. Use of such closed vesicle in making the DDS into practical application, however, is associated with various problems which need to be overcome, and critical challenges have been escape from the biological recognition mechanism for a foreign substance and in vivo control of the pharmacokinetics. In other words, delivery of the closed vesicle to the target site at high selectivity is achieved only when the stability of the closed vesicle in the blood is secured by eliminating capturing of the closed vesicle in the reticuloendothelial system (RES) such as liver and spleen and avoiding aggregation of the closed vesicle by the interaction (adsorption) with opsonin protein or plasma protein in the blood.

One known method of obviating such problems is modification of the membrane with a hydrophilic macromolecule. Closed vesicle, and in particular, liposomes modified with a hydrophilic macromolecule have been developed for use in clinical practice since they have realized high retentivity in blood, and hence, passive accumulation in the tissues having an increased vascular permeability, for example, in the tumor tissue or in the inflammatory site (see Patent Documents 1 to 3 and Non-patent Documents 3 to 5). A typical preferable modifier used in such modification with the hydrophilic practice is a derivative of polyethylene glycol (PEG) produced by attaching a lipid such as a phospholipid or a cholesterol to the polyethylene glycol. An example of the commercially available versatile modifier is a derivative of polyethylene glycol produced by attaching a phospholipid such as diacylphosphatidyl ethanolamine to the polyethylene glycol.

The liposome which is subject to such modification is a closed vesicle formed from a lipid bilayer having an aqueous phase (an internal aqueous phase) encapsulated in its interior. Various liposomes having different layer structures are known in the art, and exemplary liposomes include unilamellar vesicles such as a small unilamellar vesicle (SUV) and a large unilamellar vesicle comprising a single layer of a lipid bilayer and a multilamellar vesicle (MLV) comprising two or more layers. Use of a liposome with a MLV structure for prevention of leakage of the encapsulated drug therein have been proposed (see Patent Document 4).

Encapsulation of the drug in the liposome as described above may be accomplished by various methods, and a method known in the art capable of encapsulating the drug at a high concentration is the method using ion gradient such as pH gradient (see Patent Documents 5 to 7 and Non-patent Document 6).

[Patent Document 1] JP-5-505173-A
[Patent Document 2] JP-7-20857-B
[Patent Document 3] JP-2667051-B
[Patent Document 4] WO 01/000173
[Patent Document 5] U.S. Pat. No. 5,077,056
[Patent Document 6] JP-2847065-B
[Patent Document 7] JP-2659136-B

[Non-patent Document 1] Cancer Lett., 1997, 118(2), p. 153
[Non-patent Document 2] Br. J. Cancer., 1997, 76(1), p. 83
[Non-patent Document 3] D. D. Lasic, "LIPOSOMES from Physics to Applications", Elsevier, 1993
[Non-patent Document 4] Martin C. Woodle and Gerrit Storm ed., "Long Circulating Liposomes: Old Drugs, New Therapeutics", Springer, 1997
[Non-patent Document 5] D. D. Lasic and D. Papahadjopoulos ed., "Medical Applications of LIPOSOMES", Elsevier, 1998
[Non-patent Document 6] G. Gregoriadis ed., "Liposome Technology Liposome Preparation and Related Techniques" 2nd edition, Vol. I-III, CRC Press

DISCLOSURE OF THE INVENTION

Problems to be Solved by the Invention

Some of the drugs to be loaded in the liposome are unstable at a pH in the range higher than the neutral pH, and in such a case, the internal aqueous phase of the liposome should be kept in acidic state whether the drug is encapsulated in the lipid bilayer or in the internal aqueous phase. When a weakly basic drug is to be encapsulated (loaded) in the liposome by using a pH gradient, the internal aqueous phase is brought to acidic condition at a pH of about 4 with a citrate buffer solution and heated to a temperature equal to or higher than the phase transition temperature of the main membrane component (for example, about 60° C.). However, when the interior of the liposome is kept in acidic condition, and as the case may be, exposed to a high temperature, there is a serious concern that the stability is impaired during the manufacture or storage by the deterioration of the liposome membrane. Focusing on this problem, the inventors of the present invention produced a series of liposome preparations in which a drug which needs to be kept in an acidic condition was loaded in a liposome having a membrane modified with a hydrophilic macromolecule, and evaluated such liposome preparations for their storage stability. It was then found that in some of the liposomes modified with the hydrophilic macromolecule, decomposition of the drug was more likely to occur during the manufacture or the storage compared to the unmodified liposomes, and such decomposition of the drug, in turn, invited loss of the storage stability of the liposome preparation. In view of such finding, an object of the present invention is to provide a liposome preparation in which a high membrane stability and a high storage stability have been realized without losing the effect of membrane modification enabled by the use of the hydrophilic macromolecule when a drug should be kept in an acidic condition due to the requirement of the drug itself or due to the drug encapsulation method is loaded in a liposome having its membrane modified with a hydrophilic macromolecule.

Means to Solve the Problems

In view of the situation as described above, the inventors of the present invention made further investigation on a liposome preparation which has been produced by using a phospholipid commonly used in the art for the main membrane component and further modifying its membrane with a hydrophilic macromolecule, and then encapsulating a drug which needs to be kept in an acidic environment in its interior aqueous phase. It was then found that that lipid is hydrolyzed by the acidic environment of the internal aqueous phase, and the storage stability of the liposome preparation is thereby impaired. Based on such finding, the inventors further found that the liposome preparations which easily lose the storage stability are those having both the exterior and the interior surfaces of the membrane modified with the hydrophilic macromolecule. The inventors then gave thought to that the situation should be improved if only the exterior surface of the liposome were modified with the hydrophilic macromolecule, and confirmed that the liposome preparation having structure retains its storage stability even when the internal aqueous phase is under an acidic condition. The inventors also found that modification of the membrane with a basic compound (cationating agent) containing amino group, amidino group, or guanidino group has the effect of stabilizing the liposome membrane even if the internal aqueous phase were under an acidic condition, and a liposome preparation containing such basic compound as its membrane component exhibits excellent storage stability. The present invention as described below has been completed on the bases of such findings.

(1) A liposome preparation comprising a unilamellar vesicle formed from a lipid bilayer comprising a phospholipid as the main membrane component, and an interior aqueous phase in the vesicle at a pH of up to 5, wherein the liposome has a drug loaded therein, and wherein the vesicle is modified with a hydrophilic macromolecule only on its exterior surface.

(2) The liposome preparation according to the above (1) wherein the drug is the one which is unstable at a pH higher than 5.

(3) The liposome preparation according to the above (1) or (2) wherein the drug loaded is at a concentration of 0.05 mole/mole lipid.

(4) The liposome preparation according to the above (1) or (2) wherein the drug loaded is at a concentration of 0.1 mole/mole lipid.

(5) The liposome preparation according to any one of the above (1) to (4) wherein the main membrane component is a phospholipid having a phase transition temperature of at least 50° C.

(6) The liposome preparation according to any one of the above (1) to (5) wherein the phospholipid is a hydrogenated phospholipid.

(7) The liposome preparation according to any one of the above (1) to (5) wherein the phospholipid is a sphingophospholipid.

(8) The liposome preparation according to any one of the above (1) to (7) wherein the lipid bilayer further comprises a lipid other than the phospholipid as its membrane component.

(9) The liposome preparation according to the above (6) or (7) wherein the lipid bilayer further comprises a cholesterol as its component.

(10) The liposome preparation according to any one of the above (1) to (9) wherein the lipid bilayer further comprises a basic compound containing a group selected from amino group, amidino group, and guanidino group as its component.

(11) The liposome preparation according to the above (10) wherein the basic compound is 3,5-dipentadecyloxybenzamidine hydrochloride.

(12) The liposome preparation according to any one of the above (1) to (11) wherein the hydrophilic macromolecule is polyethylene glycol having a molecular weight of 500 to 10,000 Dalton.

(13) The liposome preparation according to any one of the above (1) to (12) wherein the hydrophilic macromolecule is introduced as a phospholipid or cholesterol derivative of the macromolecule.

(14) The Liposome preparation according to any one of the above (1) to (13) wherein the liposome preparation has an average size of 40 to 140 nm.

(15) The liposome preparation according to any one of the above (1) to (13) wherein the liposome preparation has an average size of 50 to 130 nm.

(16) The liposome preparation according to any one of the above (1) to (13) wherein the liposome preparation has an average size of 60 to 120 nm.

(17) The liposome preparation according to any one of the above (1) to (16) wherein the interior aqueous phase has a pH of 2 to 5.

(18) A method for producing a liposome preparation of the above (1) comprising the steps of preparing a vesicle having a unilamellar layer structure of a lipid bilayer containing a phospholipid so that the interior aqueous phase has a pH of up to 5;

adding a lipid derivative of the hydrophilic macromolecule to modify only the exterior surface of the vesicle; and encapsulating the drug in the interior of the liposome either by preliminarily adding the drug to the interior aqueous phase in the course of the preparation of the vesicle, or alternatively, by adding the drug from the exterior of the vesicle after preparing the vesicle by penetration through the lipid bilayer.

(19) A method for producing a liposome preparation of the above (18) wherein the drug is encapsulated by means of ion gradient method after the preparation of the vesicle by permeation through the lipid bilayer.

Effects of the Invention

The effect of modifying the membrane of the liposome with the hydrophilic macromolecule at a lower modification rate relative to the overall membrane can be higher in the case of the liposome as described above having the particular structure compared to the case of the liposome having both of the interior and the exterior surfaces modified with the hydrophilic macromolecule. More specifically, since it is free from the unnecessary modification, the liposome membrane is highly stable, and simultaneously, hydrolysis of the lipid in the internal aqueous phase in an acidic environment can be suppressed. The liposome preparation of the present invention has an excellent storage stability since unnecessary components in terms of drug structure is adequately omitted in the internal aqueous phase which is maintained in acidic state due to the constraints as described above, and unnecessary hydrolysis of the lipid is thereby suppressed to suppress the decomposition of the drug during the manufacture and storage and enable stable loading of the drug at a high concentration while retaining the effect inherent to the membrane modification such as high blood retentivity. Owing to such properties, the liposome preparation of the present invention is highly effective for treatment and/or diagnosis of a disease.

BEST MODE FOR CARRYING OUT THE INVENTION

Figure 1:
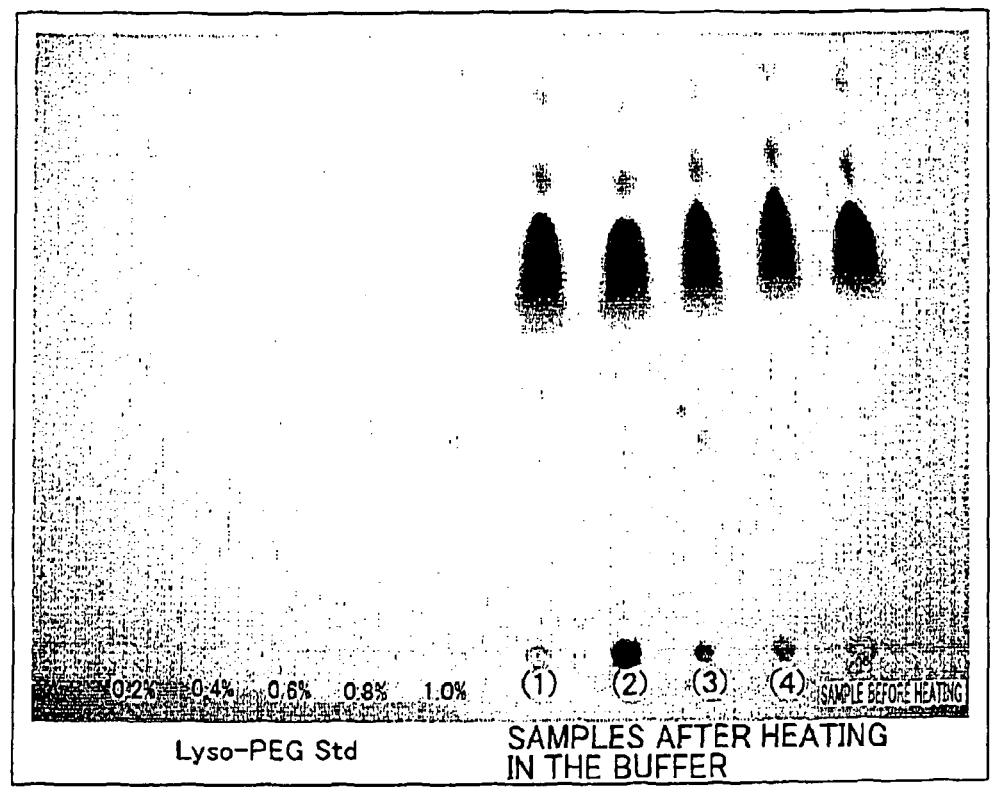
FIG. 1 shows the TLC image after the stability test of a lipid derivative of the hydrophilic macromolecule ($PEG_{5000}$-DSPE).

Next, the present invention is described in further detail.

A liposome is a closed vesicle comprising a phospholipid bilayer, and it contains an aqueous phase (internal aqueous phase) in the interior space of the vesicle. A liposome preparation is a preparation accompanied such liposome as a carrier with a drug loaded therein. As described above, known liposomes include a unilamellar (monolayer) vesicle (SUV, LUV) comprising a single lipid bilayer and a multilamellar vesicle (MLV) comprising two or more lipid bilayers, and among these, use of an LUV (large unilamellar vesicle) is particularly preferable and use of an SUV (small unilamellar vesicle) is also preferable.

In the present invention, the unilamellar vesicle typically comprises at least 50%, and preferably comprises at least 80% of the total vesicles constituting the liposome preparation.

In the present invention, the liposome used for the loading of the drug contains an internal aqueous phase at a pH of up to 5, and the unilamellar lipid bilayer has a particular membrane modification structure in which only the exterior surface is selectively modified with a hydrophilic macromolecule.

Such lipid bilayer contains at least a phospholipid as its main component.

A phospholipid is an amphipathic substance which generally contains a hydrophobic group comprising a long chain alkyl group and a hydrophilic group comprising a phosphoric acid group in one molecule. Exemplary phospholipids which may be used in the present invention include glycerophospholipids such as phosphatidylcholine (=lecithin), phosphatidylglycerol, phosphatidic acid, phosphatidylethanolamine, phosphatidylserine, and phosphatidylinocitol; sphingophospholipids such as sphingomyelin (Sphingomyelin); natural or synthetic diphosphatidyl phospholipids such as cardiolipin, and derivatives thereof; and any of such phospholipid which has been hydrogenated by a method commonly used in the art (for example, hydrogenated soybean phosphatidyl choline). The phospholipids as mentioned above is hereinafter occasionally referred to as "phospholipids".

Among these, the preferred are hydrogenated phospholipids such as hydrogenated soybean phosphatidyl choline (HSPC) and sphingomyelins (SM).

The liposome may contain either single phospholipid or a plurality of phospholipids as its main membrane component.

The liposome used is preferably the one produced by using a phospholipid having a phase transition temperature which is higher than the temperature in the body (35 to 37° C.) for the main membrane component since use of such phospholipid prevents unguarded leakage of the drug encapsulated in the liposome during the storage or in blood or in the body. Such liposome is preferably produced at a temperature higher than the phase transition temperature of the main membrane component since control of the liposome size is difficult at a temperature not exceeding the phase transition temperature of the main membrane component. For example, when the phase transition temperature of the main membrane component is near 50° C., the manufacture is preferably carried out at approximately 50 to 80° C., and more specifically, a manufacture at approximately 60 to 70° C. is preferable.

As long as the liposome of particular form according to the present invention can be produced, the liposome may also contain a membrane component other than the main membrane component as described above. For example, it is preferable to prepare a lipid mixture from the phospholipid and a lipid other the phospholipid or a derivative of such lipid (hereinafter sometimes referred to as "additional lipid") to thereby form the membrane from such lipid mixture.

Exemplary such additional lipids include a lipid which is free from the phosphoric acid, and non-limiting examples include a glyceroglycolipid, a sphingoglycolipid, and a sterol such as cholesterol which is used as a stabilizer as will be described later, and hydrogenated derivatives thereof. The liposome is preferably formed from a membrane of a lipid mixture containing additional lipids together with the phospholipid main membrane component.

In the entire membrane lipids constituting the lipid bilayer, the phospholipid which is the main membrane component typically constitutes 20 to 100% by mole, and preferably 40 to 100% by mole.

In the meanwhile, the additional lipid typically constitutes 0 to 80% by mole, and preferably 0 to 60% by mole of the entire membrane lipids.

In the present invention, the exterior side of the lipid bilayer as described above is selectively modified with a hydrophilic macromolecule. Exemplary non-limiting hydrophilic macromolecules include polyethylene glycol, polyglycerin, polypropylene glycol, Ficoll, polyvinyl alcohol, styrene-maleic anhydride alternating copolymer, divinyl ether-maleic anhydride alternating copolymer, polyvinylpyrrolidone, polyvinylmethylether, polyvinylmethyloxazoline, polyethyloxazoline, polyhydroxy-propyloxazoline, polyhydroxypropylmethacrylamide, polyumethacrylamide, polydimethylacrylamide, polyhydroxypropyl methacrylate, polyhydroxyethyl acrylate, hydroxymethylcellulose, hydroxyethylcellulose, polyaspartamide, and synthetic polyamino acid.

The hydrophilic macromolecule is preferably the one in which the end which is not bonded to the lipid has been alkoxylated (for example, by methoxylation, ethoxylation, or propoxylation) in view of improving the storage stability.

Among these, the preferred are polyethylene glycol (PEG), polyglycerin (PG), and polypropylene glycol (PPG) in view of realizing prolonged retentivity of the liposome preparation in blood.

PEG is not particularly limited for its molecular weight. PEG, however, may typically have a molecular weight of 500 to 10,000 Daltons, preferably 1,000 to 7,000 Daltons, and more preferably 2,000 to 5,000 Daltons.

PG is not particularly limited for its molecular weight. PG, however, may typically have a molecular weight of 100 to 10000 Daltons, preferably 200 to 7000 Daltons, and more preferably 400 to 5000 Daltons.

PPG is not particularly limited for its molecular weight. PPG, however, may typically have a molecular weight of 100 to 10,000 Daltons, preferably 200 to 7,000 Daltons, and more preferably 1,000 to 5,000 Daltons.

Among these, the most preferable is polyethylene glycol in view of the remarkable versatility and its effect of realizing prolonged retentivity in blood.

Polyethylene glycol is a straight chain macromolecule which has a repetitive unit of —$(CH_2CH_2O)_n$—. Since polyethylene glycol is a macromolecule having a amphipathic property, namely, since polyethylene glycol is soluble both in water and an organic solvent, and since it also has low toxicity, it is widely used for stabilizing drugs and in improving in vivo kinetics of the drugs. A carrier (such as liposome) modified with such polyethylene glycol known for the low toxicity having a drug loaded therein (for example, a liposome preparation) is highly safe.

In the present invention, the term "retentivity in blood" means that the drug is still enclosed in its carrier, and the carrier having the drug enclosed therein is still present in the blood of the host to which it has been administered.

As soon as the drug is released from the liposome, it will swiftly disperse into the blood to be exposed to the blood. When the carrier used is the one with prolonged retentivity in blood, drug administration can be accomplished by using the drug of minimal dose.

In the present invention, the term "exposure" means that the drug released to the exterior from the carrier gives some action on the external environment. More specifically, the released drug exerts its action (for example, an antitumor action) after approaching its target site and becoming in contact with such site. When the drug acts at the target site, the expected action of the drug, for example, a local action on the cells at the target site which are in the DNA synthesis phase of the cell cycle is realized at the very site.

Such a liposome car be produced as will be described below by producing an unmodified liposome comprising a unilamellar vesicle having a lipid bilayer, and thereafter selectively modifying the exterior surface of the lipid bilayer from the exterior side of the lipid bilayer with a hydrophilic macromolecule. When a derivative of the hydrophilic macromolecule is used for the modifier in introducing the hydrophilic macromolecule, the hydrophilic macromolecule will be distributed on the exterior surface of the lipid bilayer of the liposome since the hydrophobic moiety of the macromolecule will be embedded and stably held in the lipid bilayer and the hydrophilic moiety of the macromolecule will protrude outward from the exterior surface.

The lipid (hydrophobic moiety) of the lipid derivative of the hydrophilic macromolecule is not particularly limited, and the examples include a compound having a hydrophobic domain (a hydrophobic compound). Exemplary hydrophobic compounds include lipids such as the phospholipid and the additional lipid such as a sterol which constitute the lipid mixture as will be described below, or a straight chain aliphatic alcohol, a straight chain aliphatic amine, and a glycerin fatty acid ester. Among these, use of a phospholipid constitutes a preferable embodiment.

The acyl chain included in the phospholipid is preferably a saturated fatty acid, and it may preferably have a length of $C_{14}$-$C_{20}$, and more preferably, a length of $C_{16}$-$C_{18}$. Exemplary such acyl chains include dipalmitoyl, distearoyl, and palmitoyl stearoyl.

The phospholipid is not particularly limited, and exemplary phospholipids are those having a functional group which can react with the hydrophilic macromolecule as described above. Examples of the phospholipid having a Junctional group reactive with the hydrophilic macromolecule include phosphatidyl ethanolamine having amino group, phosphatidylglycerol having hydroxy group, and phosphatidylserine having carboxy group. In the preferred embodiment, the phospholipid used is phosphatidylethanolamine.

The lipid derivative of the hydrophilic macromolecule is derived from the hydrophilic macromolecule and the lipid. Combination of the hydrophilic macromolecule and the lipid is not particularly limited, and any desired combination can be used depending on the intention of its use. Exemplary combinations include a derivative of a hydrophilic macromolecule formed by the bonding of at least one member selected from the phospholipid, the additional lipid such as sterol, a straight chain aliphatic alcohol, a straight chain aliphatic amine, and a glycerin fatty acid ester and at least one member selected from PEG, PG, and PPG. When the hydrophilic macromolecule is PEG, the lipid is selected in the preferred embodiment from the phospholipid and the cholesterol. The lipid derivatives of PEG formed by such combination include phospholipid derivative of PEG and cholesterol derivative of PEG.

The lipid derivative of the hydrophilic macromolecule can be designed to have a positive charge or a negative charge, or to be neutral by the selection of the lipid. For example, when the lipid selected is DSPE, the resulting lipid derivative will have a negative charge due to the phosphate group, whereas selection of the cholesterol for the lipid will lead to the production of a neutral lipid derivative. The lipid may be adequately selected depending on the intention of the lipid introduction.

Among such lipid derivatives of the hydrophilic macromolecule, use of a phospholipid derivative of PEG is preferable in the present invention. An example of such phospholipid derivative of PEG is polyethylene glycol-distearoylphosphatidylethanolamine (PEG-DSPE). Use of the PEG-DSPE is preferable since it is a readily available versatile compound.

Such lipid derivative of the hydrophilic macromolecule may be used by a method known in the art. For example, a phospholipid derivative of PEG which is an example of the lipid derivative of the hydrophilic macromolecule may be synthesized, for example, by catalytically reacting a phospholipid having a functional group which can react with the PEG with the PEG. Exemplary catalysts which may be used in such catalytic reaction include cyanuric chloride, carbodiimide, an acid anhydride, and glutaraldehyde. The phospholipid derivative of PEG is obtained by such reaction through formation of a covalent bond between the functional group and the PEG.

In the present invention, the liposome may contain such hydrophilic macromolecule or the lipid derivative of such hydrophilic macromolecule either alone or in combination of two or more.

The modification rate of the membrane lipid (total lipid) by the lipid derivative of the hydrophilic macromolecule is typically 0.1 to 20% by mole, preferably 0.1 to 5% by mole, and more preferably 0.5 to 5% by mole in terms of the modification rate in relation to the membrane lipid. When the drug encapsulated does not need prolonged retentivity in blood as in the case of a drug to be acted in liver, the liposome preparation is preferably designed so that the modification rate is in the range of 0.25 to 5% by mole in view of improving the storage stability of the liposome preparation.

The "total lipid" used herein is the total content of the lipids constituting the membrane other than the lipid derivative of the hydrophilic macromolecule, and more specifically, the "total lipid" includes both the phospholipid and the additional lipid. When another surface modifier is used, such another surface modifier is also included in the "total lipid".

The liposome surface modified with such lipid derivative of the hydrophilic macromolecule prevents adsorption of opsonin protein and the like in the plasma onto the surface of such liposome, and this in turn improves stability of the liposome in blood and avoids capturing of the liposome in the RES, thereby improving the delivery to the target tissue or the target cell.

In the present invention, the liposome is particularly produced under the conditions such that the hydrophilic macromolecule is distributed only on the exterior surface of the liposome, and the outer membrane of the lipid bilayer is selectively modified by a hydrophilic macromolecule. In such liposome, the hydrophilic macromolecule chain on the surface of the exterior membrane extends outwardly from the liposome, while such hydrophilic macromolecule chain is substantially absent in the internal aqueous phase since the interior surface of the internal membrane of the lipid bilayer is not modified. Stability of the membrane is secured in the structure having such distribution of the hydrophilic macromolecule even if the internal aqueous phase is kept under an acidic condition compared to the structure having the hydrophilic macromolecule distributed on opposite surfaces of the exterior and interior surfaces of the bilayer. In addition, stability in blood is realized with a smaller amount of the hydrophilic macromolecule compared to the structure having the hydrophilic macromolecule on opposite surfaces of the exterior and interior surfaces of the bilayer.

In addition to the phospholipid, the additional lipid, the hydrophilic macromolecule or its lipid derivative, the liposome of the present invention may also contain an additional membrane component which is compatible with the liposome as long as the membrane structure as described above is retained and at a content not adversely affecting the object of the present invention.

Exemplary such additional membrane components include a surface modifier other than the hydrophilic macromolecule which brings change in the physical properties of the lipid to impart a desired property with the membrane of the carrier. Non-limiting examples of such additional surface modifier include a lipid having a compound other than the hydrophilic macromolecule bonded thereto.

Exemplary non-limiting compounds other than the hydrophilic macromolecule include water-soluble polysaccharides such as glucuronic acid, sialic acid, dextran, pullulan, amylose, amylopectin, chitosan, mannan, cyclodextrin, pectin, and carageenan; compounds having an acidic functional group; and basic compounds having a basic functional group such as amino group, amidino group, and guanidino group.

Among such compounds, the liposome of the present invention may have a basic compound incorporated therein as a substance which suppresses hydrolysis of the lipid. A lipid is generally known to undergo hydrolysis depending on the temperature and pH. A fatty acid ester at Sn-1 position and Sn-2 position is particularly susceptible to hydrolysis which produces a lysolipid and a fatty acid (see Grit et al., Chem. Phys. Lipids 64, 3-18, 1993). Such degradation products disturb original lipid composition resulting in an increased permeability of the lipid layer to thereby impair the stability of the liposome.

Accordingly, when a drug which should be maintained in an acidic environment is to be retained in the internal aqueous phase, stability of the lipid in the acidic environment should be improved. In the present invention, hydrolysis of the lipid can be suppressed by incorporating a basic compound in the membrane to thereby impart positive charge with the liposome surface.

The basic compound used is not particularly limited, and examples include amine compounds (including ammonium salts) such as octadecylamine CODA), N-methyl-n-octadecylamine (MODA), N,N-dimethyl-n-octadecylamine (DMODA), and stearyltrimethylammonium bromide (TMODA). A lipid derivative having quaternary ammonium salt such as TMODA is preferable in view of its capability of imparting a positive charge to the surface of the lipid layer at a low concentration.

Further examples of the basic compound include DOTMA disclosed in JP-A 61-161246, DOTAP disclosed in JP-A 5-508626, Transfectam disclosed in JP-A 2-292246, TMAG disclosed in JP-A 4-108391, 3,5-dipentadecyloxybenzamine hydrochloride disclosed in WO 97/42166, DOSPA, TfxTM-50, DDAB, DC-CHOL, and DMRIE.

When the additional surface modifier is a substance comprising a lipid and a compound having a basic functional group bonded to the lipid, this substance is called a cationized lipid. The lipid moiety of the cationized lipid is stably held in the lipid bilayer of the liposome, and the moiety of the basic functional group will be located on the surface of the membrane surface (on the surface of the outer membrane and/or on the surface of the inner membrane) of the lipid bilayer of the carrier. Modification of the membrane with the cationized lipid improves adhesion of the liposome membrane and the cell.

In the present invention, the interior aqueous layer of the liposome is at a pH of 5 or less, preferably at a pH of 2 to 5, more preferably at a pH of 3 to 5, and most preferably at a pH of about 4. Accordingly, this enables loading in the liposome of a drug which becomes unstable at a pH in excess of 5. The pH of the internal aqueous phase may be adjusted in the manufacture of the liposome by using a buffer at a physiologically acceptable pH range.

Various drugs may be loaded in the liposome as described above. Exemplary therapeutic agents include nucleic acid, polynucleotide, gene, and analogs thereof; anticancer agent, antibiotic, enzyme, antioxidant, lipid intake inhibitor, hormone, anti-inflammatory, steroid, vasodilator, angiotensin converting enzyme inhibitor, angiotensin receptor antagonist, inhibitor for smooth muscle cell growth and migration, platelet aggregation inhibitor, anticoagulant, inhibitor for release of chemical mediator, promoter or inhibitor for endothelial cell growth, aldose reductase inhibitor, inhibitor for mesangium cell growth, lipoxygenase inhibitor, immunosuppressive, immunostimulant, antiviral agent, Maillard reaction suppressor, amyloidosis inhibitor, nitric oxide synthetic inhibitor, AGEs (Advanced glycation endproducts) inhibitor, radical scavenger, protein, peptide; glycosaminoglycan and derivatives thereof; and oligosaccharide, polysaccharide, and derivatives thereof.

The liposome preparation of the present invention is capable of stably loading a drug which becomes stable at a pH not less than 5. Exemplary such drugs include dopamine hydrochloride, gabexate mesylate, norepinephrine, bromhexine hydrochloride, metoclopramide, epinephrine, vitamin B1, vitamin B6, carboplatin, gemcitabine hydrochloride, vinorelbine tartrate, vincristine sulfate, doxorubicin hydrochloride, epirubicin hydrochloride, and daunorubicin hydrochloride.

Exemplary diagnostic drugs include in vivo diagnostics such as an X ray contrast medium, a diagnostic agent for ultrasound, an isotope-labeled agent for diagnosis by nuclear medicine, and an agent for diagnosis by nuclear magnetic resonance. Other drugs which may be encapsulated in the liposome of the present invention include drugs which does not adversely affect the membrane form of the liposome of the present invention and which is not affected by inclusion in or contact with the liquid component at a pH of up to 5, and any desired drug may be loaded as long as it is adequate for encapsulation in an internal aqueous phase at a pH of up to 5 whether the drug is therapeutic or diagnostic.

The desired amount of the drug loaded in the liposome varies depending on the type of the drug. However, it is preferable that the drug can be loaded in the liposome at a high loading efficiency. In the present invention, loading of the drug at a high concentration is realized by using ion gradient.

Amount of the drug loaded in the liposome preparation of the present invention is preferably at least 0.05 mole drug/mole lipid, and more preferably, at least 0.1 mole drug/mole lipid in terms of the drug concentration in relation to the total lipid in the liposome lipid bilayer. The term "total lipid" includes all lipids constituting the liposome lipid bilayer except for the lipid derivative of the hydrophilic macromolecule, and more specifically, the "total lipid" includes the phospholipid and the additional lipid, and when the liposome contains additional surface modifier, such additional surface modifier is also included in the "total lipid".

In the present invention, the term "loading" is basically used to designate the state in which the drug is encapsulated in the closed space of the liposome (carrier). However, it may also include the state in which a part of the drug is confined in the membrane or the state in which the drug is attached to the exterior surface of the membrane.

The liposome of the present invention preparation may also contain a pharmaceutically acceptable stabilizer and/or antioxidant depending on the administration route.

Non-limiting examples of the stabilizer include sugars such as glycerol, mannitol, sorbitol, lactose, and sucrose. When a sterol such as cholesterol is used for the additional lipid constituent of the membrane, such sterol also acts as a stabilizer.

Non-limiting examples of the antioxidant include ascorbic acid, uric acid, and a tocopherol analogues (for example, vitamin E), and in the case of tocopherol, any one of the 4 isomers, namely, $\alpha, \beta, \gamma, \delta$ isomers is acceptable in the present invention. The stabilizer and/or the antioxidant used may be selected from those as described above and other agents depending on the dosage form. In addition, the stabilizer and/or the antioxidant may be respectively used either alone or in combination of two or more. In view of preventing the oxidation, the dispersion is preferably packaged by filling with nitrogen gas.

The liposome of the present invention preparation may also contain a pharmaceutically acceptable additive depending on the administration route. Examples of such additive include water, physiological saline, pharmaceutically acceptable organic solvent, collagen, polyvinyl alcohol, polyvinylpyrrolidone, carboxyvinyl polymer, sodium carboxymethyl cellulose, poly(sodium acrylate), sodium alginate, water soluble dextran, sodium carboxymethyl starch, pectin, methylcellulose, ethylcellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, PBS, in vivo degradable polymer, serum-free medium, pharmaceutically acceptable surfactant, and the buffer at a physiological pH acceptable in the living body as described above.

The additive incorporated may be adequately selected from the non-limiting additives as described above which may be incorporated alone or in combination of two or more.

The liposome preparation of the present invention is not particularly limited for its size. However, when the liposome preparation is spherical or approximately spherical, its outer diameter is 70 nm to 140 nm, preferably 80 nm to 130 nm, and more preferably 90 nm to 120 nm in the case of the LUV, and 40 nm to 140 nm, preferably 50 to 130 nm, and more preferably 60 to 120 nm in the case of the SUV.

The liposome outer diameter is the average of the entire liposome preparation measured by dynamic light scattering, and more specifically, the liposome outer diameter was measured in the present invention with Zetasizer (3000HS or S ZEM 5002 manufactured by Malvern Instruments).

In the manufacture of the liposome preparation, the final sterilization is accomplished by filtration sterilization. For such filtration sterilization, the liposome should be well smaller than the bacterium used for the standard, namely, Brevundimonas diminut with the size of about 0.3×0.8 μm since it is required in the sterilization that the liposome passes through the filter while the Brevundimonas diminut is trapped by the filter. Manufacture of such liposome having a diameter near 100 nm is important also in view of improving the reliability of the filtration sterilization.

In the present invention, the liposome preparation of the embodiment also containing the additives as described above is provided as a pharmaceutical composition. The pharmaceutical composition of the present invention is stored by the method commonly used in the art, for example, by storage at a low temperature of 0 to 8° C., or by room temperature storage at 1 to 30° C.

Next, preferable methods which may be used in manufacturing the liposome of particular structure according to the present invention are described. The manufacture methods, however, are not limited to such methods.

For example, a liposome dispersion may be produced by mixing the membrane-constituting components such as the phospholipid in a flask by using an organic solvent such as chloroform, removing the organic solvent by distillation and vacuum drying the residue to form a thin layer on the interior surface of the flask, adding the solution corresponding to the interior aqueous phase of the resulting liposome to the flask, and vigorously agitating the flask content to form the liposome dispersion. The pH of the internal aqueous phase of the liposome may be adjusted by adding a pH adjusting agent to the solution of the internal aqueous phase to thereby adjust the pH to the desired pH. Next, the thus obtained liposome dispersion is centrifuged, and the supernatant is purified by decantation to obtain the final liposome dispersion. The modification of the liposome surface with the hydrophilic macromolecule may be accomplished by the use of a derivative such as a phospholipid derivative or a cholesterol derivative of the polyethylene glycol (PEG), and such modification may be accomplished by adding the polyethylene glycol derivative or an aqueous solution of the polyethylene glycol derivative to the liposome dispersion produced as described above to thereby produce a liposome having the PEG chain only on the exterior surface of the liposome.

Alternatively, a liposome may be produced by producing a liposome containing a membrane-constituting lipid such as a phospholipid having a reactive functional group by the method commonly used in the art, and thereafter adding a PEG having one activated end to the exterior solution of the liposome for binding of such PEG to the membrane-constituting lipid such as the phospholipid having the functional group.

Furthermore, a liposome can be produced by mixing the components and injecting the mixture from a high pressure injection emulsifier at a high pressure. This method is described in detail in Terada and Yoshimura, et al., "Liposomes in life sciences", Springer-Verlag Tokyo (1992), which is herein incorporated by reference.

In the procedures as described above, various techniques are available for use in producing a liposome having the desired size ("Liposome Technology Liposome Preparation and Related Techniques" 2nd edition, edited by G. Gregoriadis, Vol. I-III, CRC Press) which is herein incorporated by reference.

The liposome dispersion may be forcedly passed through filters by using an extruder to thereby produce a dispersion containing unilamellar vesicles. This filtration is typically accomplished by using two or more filters respectively having different pore diameters, which typically include a filter having a pore diameter larger than the desired diameter and a filter for last having a pore diameter adapted for producing the liposome having the desired diameter. The percentage of the unilamellar vesicle increases with the increase in the number of extrusion through the filters having different pore diameters, and the liposome dispersion produced by such repeated filtration can be deemed as a dispersion substantially comprising unilamellar liposomes. The term "substantially comprising unilamellar liposomes" means that percentage of the unilamellar vesicles existing in the entire carriers (vesicles) constituting the liposome preparation is at least 50%, and preferably at least 80%.

The loading of the drug in such liposome may be accomplished, for example, by a method in which the lipid layer constituting the liposome is hydrated with an aqueous solution containing the drug to thereby load the drug in the liposome (passive loading), or by a method in which a ion gradient is formed between the interior and the exterior of the liposome layer so that the drug permeates through the liposome layer according to the ion gradient to become loaded in the liposome (remote loading) (see the documents cited as for the techniques for obtaining the liposome of the desired size, U.S. Pat. No. 5,192,549, and U.S. Pat. No. 5,316,771). The preferable method used in the present invention in producing the liposome preparation is the remote loading. This method is capable of realizing a high ratio of the drug to the lipid enabling the manufacture of a liposome preparation at a high loading weight which is useful in the clinical practice.

This remote loading is accomplished by forming a pH gradient between the internal aqueous phase and the external aqueous phase. The pH gradient is formed, for example, by forming the liposome by the method as described above at a low pH, and thereafter replacing the external aqueous phase.

The gradient formed across the liposome layer may be the one formed by $Na^+/K^+$ concentration gradient. The technique of introducing a drug in the preliminarily produced liposome by the remote loading by the $Na^+/K^+$ concentration gradient is described in U.S. Pat. No. 5,077,056, and the loading may be accomplished by referring to this document which is herein incorporated by reference.

The formation of the ion gradient between the interior and the exterior of the liposome layer may be accomplished by using a concentration gradient of ammonium ion or a concentration gradient of an organic compound having protonatable amino group with the higher pH on the interior side and the lower pH on the exterior side. The organic compound having protonatable amino group is preferably the one having a low molecular weight, and exemplary non-limiting examples include methylamine, ethylamine, propylamine, diethylamine, ethylenediamine, and aminoethanol.

The technique of introducing a drug in the preliminarily produced liposome by the remote loading by the concentration gradient of ammonium ion is described in U.S. Pat. No. 5,192,549, and the loading may be accomplished by referring to this document which is herein incorporated by reference. More specifically, a liposome is preliminarily produced in an aqueous buffer solution containing 0.1 to 0.3M ammonium salt (for example, ammonium sulfate), and a gradient of ammonium ion is formed by replacing the exterior medium with a medium free from the ammonium ion, for example sucrose solution. The ammonium ion in the interior will then be by equilibrated by ammonia and proton, and the ammonia will disappear by dispersion through the lipid layer. With the disappearance of the ammonia, the equilibration in the liposome continuously shift in the direction of the proton formation, and as result, the protons are accumulated in the liposome and a pH gradient is formed between the interior and the exterior of the liposome. When the drug is introduced in the dispersion of the liposomes having such pH gradient, the drug will be encapsulated in the liposome.

The ammonium salt used in forming the ammonium ion gradient is not particularly limited, and exemplary ammonium salts include ammonium sulfate, ammonium hydroxide, ammonium acetate, ammonium chloride, ammonium phosphate, ammonium citrate, ammonium succinate, ammonium lactobionate, ammonium carbonate, ammonium tartrate, and ammonium oxalate.

The pH gradient between the interior and the exterior of the liposome may also be formed by using an ionophore. The technique of forming a pH gradient between the interior and the exterior of the liposome by using an ionophore and introducing the drug in the liposome by remote loading is described in U.S. Pat. No. 5,837,282, and the drug introduction may be accomplished by referring to this document which is herein incorporated by reference.

More specifically, the pH gradient formation between the interior and the exterior of the liposome and the subsequent drug introduction by the remote loading may be carried out by the procedure as described below.

A liposome dispersion is produced by mixing the membrane-constituting components such as the phospholipid in a flask by using an organic solvent such as chloroform, removing the organic solvent by distillation and vacuum drying the residue to form a thin layer on the interior surface of the flask, adding an acidic buffer (for example, a buffer solution at pH 4), and shaking the flask. Optionally, the liposome of the desired size is collected, and a pH gradient is formed by replacing the solution in the exterior of the liposome with an exterior aqueous phase by such means as gel filtration, or alternatively, by adjusting the pH of the exterior aqueous phase of the liposome to a pH range near the neutral pH (for example, near pH 7 to 7.5) by means of an adequate pH adjusting agent. As described above, the modification of the liposome with the hydrophilic macromolecule may be conducted in the present invention either before or after the loading of the drug as long as the drug is loaded after forming the unilamellar vesicle of the lipid bilayer.

Parenteral administration routes of the liposome preparation include intravenous injection such as infusion (iv), intramuscular injection, intraperitoneal injection, and percutaneous injection, and the administration route may be adequately selected depending on the age and the symptoms of the patient. More specifically, the liposome preparation may be administered, for example, by syringe injection or by infusion of the pharmaceutical composition. Alternatively, the administration can be accomplished by inserting a catheter to the interior of the patient or host body, for example, in a body lumen such as blood vessel, and guiding the distal end of the catheter to the target site, and administering the liposome preparation through the catheter to the desired target site or the region in the vicinity of such site, or alternatively, to a site which is expected to the blood flow in the upstream of the target site.

The liposome preparation of the present invention is administered to a patient suffering from a disease at an amount sufficient for healing or at least partial healing of the symptom associated with the disease. For example, the effective dose encapsulated in the liposome preparation is generally selected from the range of 0.01 mg to 100 mg per body weight of 1 kg per day. However, the liposome preparation of the present invention is not limited to such a dose. The liposome preparation may be administered either after the onset of the disease, or before the disease onset when the onset of the disease is expected for a preventive purpose so that symptom after the onset is ameliorated. The dosage period is adequately selected depending on the age and symptoms of the patient.

EXAMPLES

Next, the present invention is described in further detail by referring to Examples and Test Examples which by no means limit the scope of the present invention.

The components used in the Examples and Test Examples had the molecular weight as described below.

Hydrogenated soybean lecithin (abbreviated as HSPC; SPC3 manufactured by Lipoid having a molecular weight of 790)

Cholesterol (abbreviated as Chol; a product manufactured by Solvay having a molecular weight of 386.65)

Sphingomyelin (abbreviated as SM; Sphingomyelin manufactured by Avanti Polar Lipidos having a molecular weight of 703.3)

Polyethylene glycol 5000-phosphatidyl ethanolamine (abbreviated as $PEG_{5000}$-DSPE; a product manufactured by NOF Corporation having a molecular weight of 6075)

3,5-dipentadecyloxybenaamine hydrochloride (having a molecular weight of 609.41)

Octadecylamine (abbreviated as ODA; a product manufactured by Tokyo Chemical Industry having a molecular weight of 269.51), N-methyl-n-octadecylamine (abbreviated as MODA; manufactured by Tokyo Chemical Industry having a molecular weight of 283.54), N,N-dimethyl-n-octadecylamine (abbreviated as DMODA; a product manufactured by Tokyo Chemical Industry having a molecular weight of 297.56), Stearyltrimethylammonium bromide (abbreviated as TMODA manufactured by Tokyo Chemical Industry having a molecular weight of 392.5), Doxorubicin (Doxorubicin Hydrochloride USP23 manufactured by BORYUNG having a molecular weight of 579.99).

Example 1

Preparation of Liposome Containing Doxorubicin

Example 1 shows preparation of the liposome of the present invention. An LUV liposome was produced by adding a lipid derivative of the hydrophilic macromolecule ($PEG_{5000}$-DSPE which is a distearoylphosphatidylethanolamine derivative of polyethylene glycol having a molecular weight of 5000 Dalton) to a liposome produced as described below under a low pH condition (pH 4) to provide a hydrophilic macromolecule (PEG chain) on the exterior surface of the exterior membrane of the liposome, and thereafter introducing a drug by ion gradient method.

Hydrogenated soybean phosphatidyl choline (HSPC) and cholesterol (Chol) were dissolved in t-butanol at a molar ratio (HSPC:Chol) of 54:46, and freeze dried to produce a mixed lipid of the membrane components.

300 mM solution of citric acid and 300 mM solution of trisodium citrate was mixed. A solution for the interior aqueous phase was prepared by adjusting the pH to 4.0, and a solution for the exterior aqueous phase was prepared by adjusting the pH to 7.5.

0.37 g of the mixed lipid produced as described above was weighed, and to this was added 10 mL of the solution of the interior aqueous phase. The mixture was placed in an incubator at 68° C. for 15 minutes for swelling, and agitated with Vortex to produced a crude dispersion of the liposome. Using an extruder (manufactured by Lipex Biomembranes) that has been heated to 68° C., the crude liposome dispersion was passed 5 times through a filter having a pore diameter of 200 nm; and after changing the filter to a filter having a pore diameter of 100 nm, the filtration procedure was repeated twice by using this filter (a filter with a pore diameter of 200 nm×5; a filter with a pore diameter of 100 nm×5; and a filter with a pore diameter of 100 nm×5) to thereby produce a LUV liposome dispersion. The sample after the extrusion was cooled in an ice bath.

The thus prepared liposome dispersion was subjected to gel filtration through a gel column (Sepharose 4 Fast Flow) that had been fully substituted with the exterior aqueous phase to thereby obtain a pH gradient. The sample after the gel filtration was cooled in an ice bath.

The lipid in the liposome after the gel filtration was quantitatively evaluated (quantitative determination of the HSPC). Based on the HSPC concentration calculated in the quantitative determination of the HSPC, $PEG_{5000}$-DSPE (manufactured by NOF Corporation) was added to a concentration of 1.0% by mole, and the mixture was agitated at 60° C. for 30 minutes to thereby introduce the $PEG_{5000}$-DSPE.

Next, amount of the doxorubicin hydrochloride was calculated based on the HSPC concentration that was calculated in the quantitative determination of the HSPC so that the ratio of the doxorubicin hydrochloride to the HSPC was 0.2 (w/w), and the required amount of the doxorubicin hydrochloride was weighed according to the calculation. A doxorubicin hydrochloride solution at 10 mg/mL was prepared using 10% sucrose solution (pH 9.0). A predetermined amount of the doxorubicin hydrochloride solution (10 mg/mL) was added to the liposome dispersion, and the mixture was stirred at 60° C. for 60 minutes to thereby introduce the doxorubicin hydrochloride in the liposome. The sample after the doxorubicin hydrochloride introduction was cooled in an ice bath. Gel filtration was conducted using a column (Sepharose 4 Fast Flow having a diameter of 2.8 cm and a length of 20 cm) fully substituted with 10% sucrose (pH 6.5) to remove the doxorubicin hydrochloride that had not been introduced in the liposome.

In Example 1, the phospholipid of the liposome was quantitatively determined using Phospholipid C-Test Wako manufactured by Wako Pure Chemical.

Concentration of the doxorubicin encapsulated in the liposome was determined by measuring absorbance at 480 nm using a spectrophotometer for the solution prepared by adding 2 mL of methanol to 40 μL of the doxorubicin liposome.

The liposome size was measured by diluting 20 μL of the liposome dispersion with physiological saline to 3 mL, and measuring average liposome diameter using Zetasizer 3000HS (Malvern Instruments). The liposome produced is shown in Table 1.

Comparative Example 1

Preparation of Liposome Containing Doxorubicin

Comparative Example 1 shows preparation of the liposome outside the scope of the present invention. The liposome preparation was produced by using the liposome components which are the same as those of Example 1 except that the hydrophilic macromolecule (PEG chain) was distributed on both sides of the inner and outer layers of the liposome bilayer by introducing the lipid derivative of the hydrophilic macromolecule ($PEG_{5000}$-DSPE) simultaneously with the liposome formation.

More specifically, 0.37 g of the lipid mixture which was the same as the one used in Example 1 (HSPC:Chol=54:46) was weighed, and based on the HSPC concentration of the lipid mixture, 0.073 g of $PEG_{5000}$-DSPE was weighed so that the PEG$_{5000}$-DSPE was at 2.0% by mole. After adding 1 mL of ethanol 1 ml, the mixture was dissolved in an incubator at 65° C. for 30 minutes. After confirming the complete dissolution, 10 mL of the interior aqueous phase was added, and the mixture was agitated by heating to 65° C. for 60 minutes to prepare the crude liposome dispersion. This crude liposome dispersion was processed with the extruder by repeating the procedure of Example 1, and the sample after the extrusion was cooled in an ice bath.

The thus prepared liposome was subjected to gel filtration by repeating the procedure of Example 1 through a gel column (Sepharose 4 Fast Flow) that had been fully substituted with the exterior aqueous phase to thereby obtain a pH gradient. The sample after the gel filtration was cooled in an ice bath.

The lipid in the liposome after the gel filtration was quantitatively evaluated (quantitative determination of the HSPC). Based on the thus determined HSPC concentration, amount of the doxorubicin hydrochloride was calculated so that the ratio of the doxorubicin hydrochloride to the HSPC was 0.2 (w/w). Based on the thus calculated amount, required amount of the doxorubicin hydrochloride was weighed, and doxorubicin hydrochloride solution at 10 mg/mL was prepared using 10% sucrose (pH 9.0).

By repeating the procedure of Example 1, a predetermined amount of the doxorubicin hydrochloride solution (10 mg/mL) was added to the liposome dispersion for introduction of the doxorubicin hydrochloride, and the doxorubicin hydrochloride that had not been encapsulated in the liposome was removed.

Amount of the phospholipid in the liposome, amount of the doxorubicin hydrochloride encapsulated in the liposome, and the liposome size were measured by repeating the procedure of Example 1. The liposome produced is shown in Table 1.

Example 2

Preparation of a Liposome Having Doxorubicin Encapsulated According to the Present Invention In producing the liposome preparation of the present invention, a mixed lipid containing sphingomyelin (SM) and Chol at a ratio of 55:45 was used for the membrane component. SM and Chol were dissolved at a molar ratio of 55:45 in a mixed solution of chloroform and methanol, and the solvent was removed by distillation at a reduced pressure to thereby leave a thin layer. 300 mM solution of citric acid and 300 mM solution of trisodium citrate were mixed, and a solution for the interior aqueous phase was prepared by adjusting this solution to pH 4.0. 0.30 g of the lipid mixture was weighed, and 5 mL of the solution for the interior aqueous phase was added to the lipid mixture, and the mixture was hydrated at 70° C. for 10 minutes. Uniform dispersion of the lipid was realized by occasionally sonicating the mixture in a bath-type sonicator that had been heated to 55° C.

Using an extruder (manufactured by Lipex Biomembranes) that has been maintained at a temperature of 65° C., the resulting lipid dispersion was passed 3 times through a filter having a pore diameter of 400 nm; another 3 times through a filter having a pore diameter of 200 nm; and after changing the filter to a filter having a pore diameter of 100 nm, repeated filtration through this filter was conducted twice (a filter with a pore diameter of 400 nm×3; a filter with a pore diameter of 200 nm×3; a filter with a pore diameter of 100 nm×5; and a filter with a pore diameter of 100 nm×5). The sample after the extrusion was cooled in an ice bath.

The thus prepared liposome was subjected to gel filtration through a gel column (Sepharose 4 Fast Flow) that had been fully substituted with physiological saline. The sample after the gel filtration was cooled in an ice bath.

The lipid in the liposome after the gel filtration was quantitatively evaluated (quantitative determination of the SM). Based on the thus SM concentration calculated in the quantitative determination of the SM, PEG$_{5000}$-DSPE was added to a concentration of 0.75% by mole, and the mixture was agitated at 60° C. for 30 minutes to thereby introduce the PEG$_{5000}$-DSPE.

Next, amount of the doxorubicin hydrochloride which corresponds to 20% by mole of the total lipid content of the liposome was calculated based on the SM concentration that was calculated in the quantitative determination of the SM and the required amount of the doxorubicin hydrochloride was weighed according to the calculation. A doxorubicin hydrochloride solution at 10 mg/mL was prepared using physiological saline. A predetermined amount of the doxorubicin hydrochloride solution (10 mg/mL) was added to the liposome dispersion, and the mixture was adjusted to pH 7.4 using 1N NaOH or saturated sodium hydrogencarbonate, and the mixture was stirred at 65° C. for 30 minutes to thereby introduce the doxorubicin hydrochloride in the liposome. The sample after the doxorubicin hydrochloride introduction was cooled in an ice bath. Gel filtration was conducted using a column (Sepharose 4 Fast Flow) fully substituted with physiological saline to remove the doxorubicin hydrochloride that had not been encapsulated in the liposome.

Amount of the phospholipid in the liposome, amount of the doxorubicin hydrochloride encapsulated in the liposome, and the liposome size were measured by the same method as Example 1. The liposome produced is shown in Table 1.

TABLE 1

| | Membrane constitution (mole ratio) | Liposome size, nm | Amount of drug loaded, mole drug/ mole lipid |
|---|---|---|---|
| Example 1 | HSPC:Chol:PEG$_{5000}$-DSPE = 54:46:1 | 118.8 | 0.11 |
| Comparative Example 1 | HSPC:Chol:PEG$_{5000}$-DSPE = 54:46:2 | 112.9 | 0.13 |
| Example 2 | SM: Chol:PEG$_{5000}$-DSPE = 54:46:0.75 | 107.4 | 0.12 |

Example 3

HSPC:Chol:3,5-dipentadecyloxybenzamine hydrochloride was dissolved in t-butanol at a molar ratio of 50/42/8, and the solution was freeze dried to obtain a lipid mixture.

300 mM solution of citric acid and 300 mM solution of trisodium citrate were mixed, and the solution was adjusted to pH 4 to thereby prepare a solution for the internal aqueous phase.

0.30 g of the lipid mixture was weighed, and 5 ml of the solution of the internal aqueous phase was adjusted to pH 4 was added, and the mixture was hydrated at 70° C. for 10 minutes. Uniform dispersion of the lipid was realized by occasionally sonicating the mixture in a bath-type sonicator that had been heated to 55° C. Using an extruder (manufactured by Lipex Biomembranes) that has been maintained at a temperature of 73° C., the resulting lipid dispersion was passed 3 times through a filter having a pore diameter of 0.4 μm; 3 times through a filter having a pore diameter of 0.2 μm;

and 10 times through a filter having a pore diameter of 0.1 μm to obtain an LUV dispersion. The resulting liposome had a size of 111.3 nm.

The thus prepared liposome dispersion was subjected to gel filtration by adding to a column (Sepharose 4 Fast Flow having a diameter of 1.5 cm and a length of 25 cm), and eluting with physiological saline, and the exterior aqueous phase was substituted with physiological saline.

$PEG_{5000}$-DSPE was dissolved in physiological saline to a concentration of 10 mg/mL, and this solution was added to the exterior aqueous phase so that the $PEG_{5000}$-DSPE constitutes 0.75% by mole of the total lipid content of the liposome, and the mixture was incubated at 60° C. for 30 minutes with stirring.

Doxorubicin was dissolved in physiological saline to a concentration of 10 mg/mL, and this solution was added so that the doxorubicin constitutes 20% by mole of the total lipid content of the liposome, and adjusted to pH 7.4 using 1N NaOH or saturated sodium hydrogencarbonate. The solution was then incubated at 65° C. for 30 minutes.

In the procedure as described above, the phospholipid of the liposome was quantitatively determined as in the case of Example 1.

The liposome size was measured by diluting 100 μL of the liposome dispersion with physiological saline to 3 mL, and measuring average liposome diameter using Zetasizer S ZEM 5002 (Malvern Instruments). Amount of the doxorubicin encapsulated in the liposome (the amount drug loaded=drug/lipid) was determined by measuring absorbance at 480 nm with a spectrophotometer for a mixture of 0.1 mL of the doxorubicin liposome with 0.3 mL of 1N HCl and 3.6 mL of isopropanol. The amount of the doxorubicin was 0.12 mol/mol.

Test Example 1

$PEG_{5000}$-DSPE (manufactured by NOF Corporation) was dissolved in each of the following 4 buffers to a concentration of 5 mg/mL, and the solution was heated at 65° C. for 90 minutes. $PEG_{5000}$-DSPE was also dissolved in the same buffer to a concentration of 10 mg/mL, and the solution was stored at 40° C. for 1 week.

Buffer (1): ammonium sulfate (250 mM)
Buffer (2): L-Histidine (10 mM), 10% sucrose, pH 6.5
Buffer (3): citric acid (300 mM), pH 4.0
Buffer (4): citric acid (300 mM), pH 7.5

Figure 2:
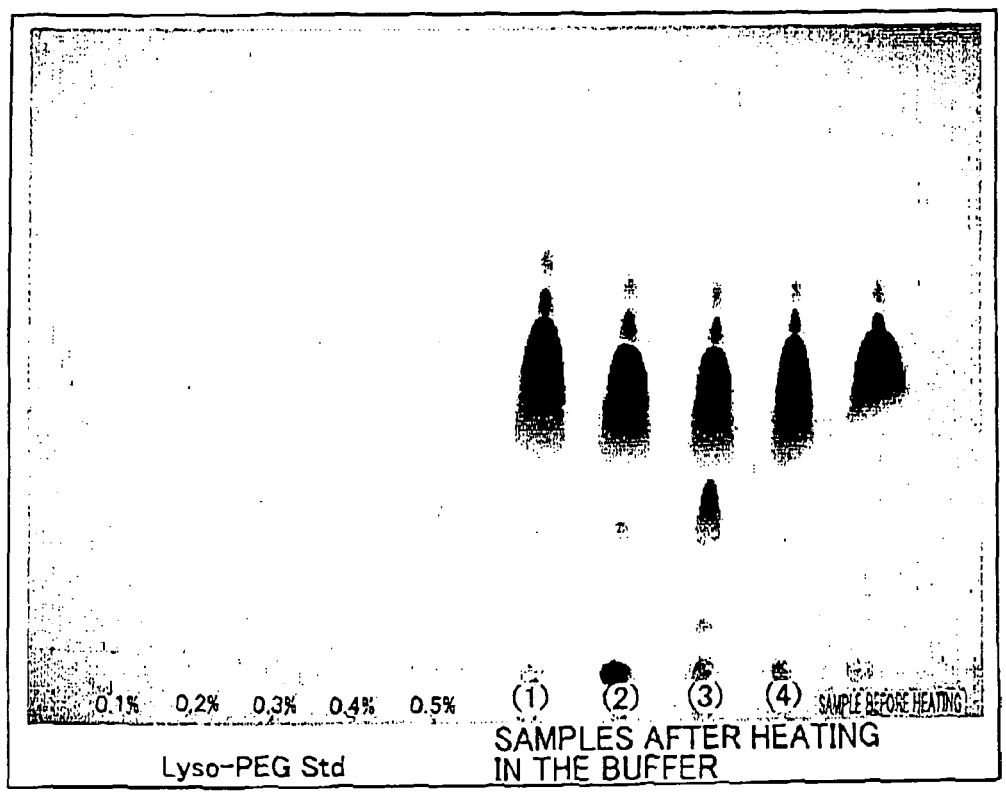
FIG. 2 shows the TLC image after the stability test of a lipid derivative of the hydrophilic macromolecule ($PEG_{5000}$-DSPE).

10 μL of the thus stored solution was spotted at a position 1 cm above the lower end of the silica gel thin layer of 20 cm×20 cm. This silica gel thin layer was then placed in a glass container that had been preliminarily equilibrated with the developing solvent which was a mixed solution of chloroform, methanol, and ammonia (28) (85:14:1) for development with the developing solvent for about 15 cm, and the degradation product was searched by iodine color development. The results of this thin layer chromatography (TLC) are shown in FIG. 1 to 2. FIG. 1 shows the results of the TLC for the $PEG_{5000}$-DSPE solution which had been heated to 65° C. for 90 minutes, and FIG. 2 shows the results of the TLC for the $PEG_{5000}$-DSPE solution which had been heated to 40° C. for 1 week. Increase in the spot was not observed at the position of the degradation product (lyso-lipid) before and after the heating (see the spot of Lyso-PEG Std) for the $PEG_{5000}$-DSPE that had been dissolved in the buffer at a pH of 5 or higher whereas increase in the spot was evident in the case of the $PEG_{5000}$-DSPE that had been dissolved in the buffer at pH 4.

Test Example 1 shows the data of stability of the lipid derivative of a hydrophilic macromolecule ($PEG_{5000}$-DSPE) under acidic conditions. The data show that the $PEG_{5000}$-DSPE is degraded when it is heated under acidic conditions (buffer (3), citric acid, pH 4.0). This in turn means that, when the liposome is produced by a method in which the $PEG_{5000}$-DSPE is kept under acidic buffer conditions as in the case of Comparative Example 1, the $PEG_{5000}$-DSPE is expected to degrade during the manufacture or the storage. In the case of the liposome produced by the method of Comparative Example 1, the internal aqueous phase is acidic, and the $PEG_{5000}$-DSPE in the region in contact with the internal aqueous phase is also expected to lyze. The results are shown in Test Example 2.

Test Example 2

Comparison of Degradation Behavior Between the Liposomes of Example 1 and Comparative Example 1

Figure 3:
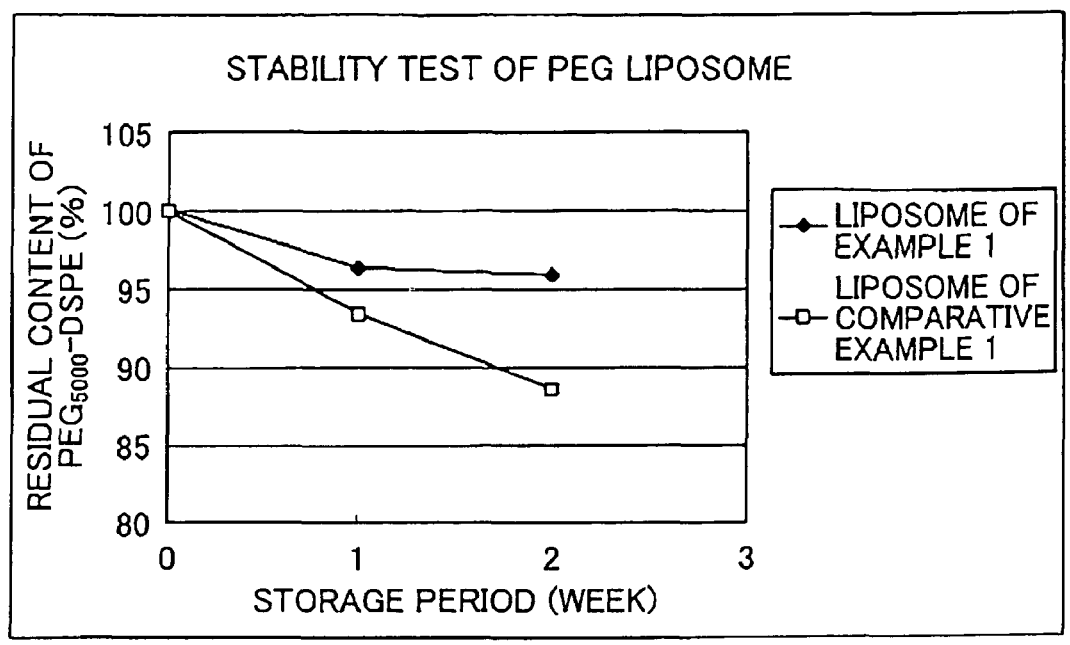
FIG. 3 is a view showing residual content of $PEG_{5000}$-DSPE in storage test.

The two types of liposomes produced in the Example 1 and the Comparative Example 1 were stored at 40° C. for 1 week or 2 weeks, and the liposomes were then evaluated for their residual content of the $PEG_{5000}$-DSPE by HPLC. The results are shown in FIG. 3 by the residual content of the $PEG_{5000}$-DSPE for the PEG liposomes stored at 4° C.

The results of the Test Example 2 demonstrate that the residual content of the $PEG_{5000}$-DSPE decreased in the case of the liposome of the Comparative Example 1 indicating the degradation of the $PEG_{5000}$-DSPE whereas no significant change in the residual content was observed in the case of the liposome of the present invention produced in Example 1 in indicating the absence of the degradation of the $PEG_{5000}$-DSPE.

When the degradation of the $PEG_{5000}$-DSPE is prevented, instabilization of the lipid bilayer, leakage of the drug introduced in the liposome, aggregation of the liposome, decrease in the effect of preventing adsorption of the liposome to plasma protein or opsonin protein, loss of liposome stability in blood, and the like associated with the degradation of the $PEG_{5000}$-DSPE are also prevented.

Example 4

Lipid were weighed so that HSPC, Chol, and a basic lipid ((1) ODA, (2) MODA, (3) DMODA, or (4) TMODA are) at a molar ratio of 50:42:8, and these lipids were dissolved in ethanol. After confirming the complete dissolution of the lipid, 9 mL of ammonium sulfate solution (250 ml) was added, and the mixture was agitated with heating to 68° C. After the completion of the agitation with heating, the dispersion was passed 5 times through a filter having a pore diameter of 200 nm at 1.0 MPa using an extruder which had been heated to 68° C., and after changing the filter to the one having a pore diameter of 100 nm, the dispersion was passed 5 times through this filter at 2.0 MPa. After changing to another filter having a pore diameter of 100 nm, the dispersion was passed another 5 times through this filter at 2.0 MPa. 2 mL of the $PEG_{5000}$-DSPE solution (36.74 mg/mL (RO water) was added to the sample after the extrusion so that rate of the $PEG_{5000}$-DSPE introduction was 0.75% by mole, and the mixture was agitated with heating to 60° C. for 30 minutes to thereby introduce the $PEG_{5000}$-DSPE. The sample after the introduction was cooled in an ice bath. Structure of the basic lipid used are shown below.

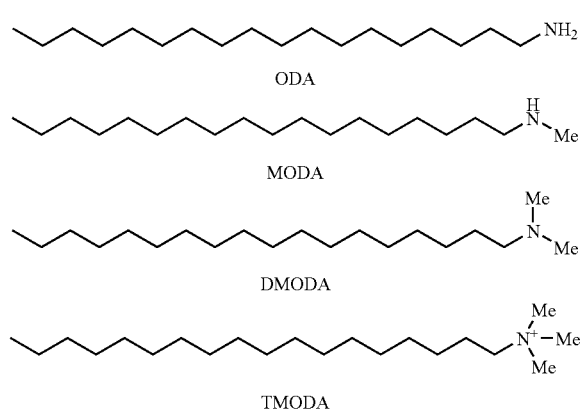

The thus prepared liposome dispersion was subjected to gel filtration through a gel column (Sepharose 4 Fast Flow) that had been fully substituted with a 10% solution of sucrose (pH 9.0) to thereby obtain a pH gradient. The sample after the gel filtration was cooled in an ice bath.

Next, amount of the doxorubicin hydrochloride was calculated based on the HSPC concentration that was calculated in the quantitative determination of the HSPC so that the ratio of the doxorubicin hydrochloride (Dox) to the total lipid (mole/mole) was 0.16 (Dox/total lipid (w/w)=0.18). Based on the calculation, the required amount of the doxorubicin hydrochloride was weighed. A doxorubicin hydrochloride solution at 10 mg/mL was prepared using 10% sucrose solution (pH 9.0). A predetermined amount of the doxorubicin hydrochloride solution (10 mg/mL) was added to the liposome dispersion, and the mixture was stirred at 60° C. for 60 minutes to thereby introduce the doxorubicin hydrochloride in the liposome. The sample after the doxorubicin hydrochloride introduction was cooled in an ice bath. Gel filtration was conducted using a column (Sepharose 4 Fast Flow having a diameter of 2.8 cm and a length of 20 cm) fully substituted with 10% sucrose (pH 6.5) to remove the doxorubicin hydrochloride that had not been encapsulated in the liposome.

The resulting liposome preparations (1) to (4) corresponding the basic lipids as described above were evaluated for the amount of the phospholipid, liposome size, and Zeta potential.

In this Example, the phospholipid of the liposome was quantitatively determined using Phospholipid C-Test Wako manufactured by Wako Pure Chemical.

The liposome size was measured by diluting 20 μL of the liposome dispersion with physiological saline to 3 mL, and measuring average liposome diameter using Zetasizer 3000HS (Malvern Instruments).

Zeta potential was measured as described below.

About 2.5 mL of RO water was introduced in a 2.5 mL syringe. By pulling the plunger, 20 μL of the liposome dispersion and 20 μL of Dulbecco's PBS were introduced from the tip of the syringe, and air was removed by pushing the plunger. The syringe was horizontally placed for mixing and uniform dispersion of the syringe content, and Zeta potential was measured using Zetasizer 3000 HS.

The measurements for the liposome preparations (1) to (4) produced in Example 4 are shown in FIG. 2 together with the measurements of the liposome preparation of Example 1.

Example 5

Lipid were weighed so that HSPC, Chol, and a basic lipid (TMODA) were at a molar ratio of (1) 53.5:45.5:1, (2) 53:45:2, (3) 52:44:4, or (4) 45.4:38.6:16, and these lipids were dissolved in ethanol. The liposomes were prepared by repeating the subsequent procedure of Example 4.

As in the case of Example 4, the resulting liposome preparations (1) to (4) corresponding the ratio of the basic lipid as described above were evaluated for the amount of the phospholipid, liposome size, and Zeta potential. The results are shown in Table 2.

TABLE 2

| | Layer constitution (molar ratio) | Liposome size, nm | Zeta potential, mV |
|---|---|---|---|
| Example 1 | HSPC:Chol:PEG$_{5000}$-DSPE = 54:46:0.75 | 110.9 | −6.1 |
| Example 4(1) | HSPC:Chol:ODA:PEG$_{5000}$-DSPE = 50:42:3:0.75 | 119.7 | 2.2 |
| Example 4(2) | HSPC:Chol:MODA:PEG$_{5000}$-DSPE = 50:42:8:0.75 | 118.2 | 1.9 |
| Example 4(3) | HSPC:Chol:DMODA:PEG$_{5000}$-DSPE = 50:42:8:0.75 | 120.3 | 2.7 |
| Example 4(4) | HSPC:Chol:TMODA:PEG$_{5000}$-DSPE = 50:42:8:0.75 | 113.1 | 4.6 |
| Example 5(1) | HSPC:Chol:TMODA:PEG$_{5000}$-DSPE = 53.5:45.5:1:0.75 | 119.0 | −3.3 |
| Example 5(2) | HSPC:Chol:TMODA:PEG$_{5000}$-DSPE = 53:45:2:0.75 | 120.6 | −3.0 |
| Example 5(3) | HSPC:Chol:TMODA:PEG$_{5000}$-DSPE = 52:45:4:0.75 | 124.3 | −1.6 |
| Example 5(4) | HSPC:Chol:TMODA:PEG$_{5000}$-DSPE = 45.4:38.6:16:0.75 | 110.3 | 5.1 |

Test Example 3

Degradation of PEG in the Liposome Preparation

The liposome preparations prepared in Examples 4 and (the liposome preparation (4) in these Examples) were stored at 40° C. for 2 weeks, and measured for the amount of the PEG$_{5000}$-DSPE by HPLC. The residual content of the PEG$_{5000}$-DSPE in relation to the PEG liposome stored at 4° C. are shown in Table 3 together with the results for the liposome preparation of Example 1 (prepared by using no basic compound) (Test Example 2). It was demonstrated that the incorporation of the basic compound suppresses the decrease in the content of the PEG$_{5000}$-DSPE in a manner dependent on the content of the basic compound.

TABLE 3

| | Layer constitution (molar ratio) | Residual content (%) of PEG$_{5000}$-DSPE |
|---|---|---|
| Example 1 | HSPC:Chol:PEG$_{5000}$-DSPE = 54:46:0.75 | 97.6 |
| Example 4(4) | HSPC:Chol:TMODA:PEG$_{5000}$-DSPE = 50:42:8:0.75 | 99.0 |
| Example 5(4) | HSPC:Chol:TMODA:PEG$_{5000}$-DSPE = 45.4:38.6:16:0.75 | 101.7 |

Test Example 4

Degradation of HSPC in the Liposome Preparation

The liposome preparations prepared in Examples 4 and 1 were stored at 40° C. for 1 week or 2 weeks, and measured for the content (%) of the degradation product of the HSPC by HPLC. The content (%) of the degradation product of the HSPC was calculated as described below.

Content of the degradation product of HSPC (%)= {(total peak area of the HSPC degradation product)/(total peak area of HSPC+total peak area of the HSPC degradation product)}×100

Figure 4:
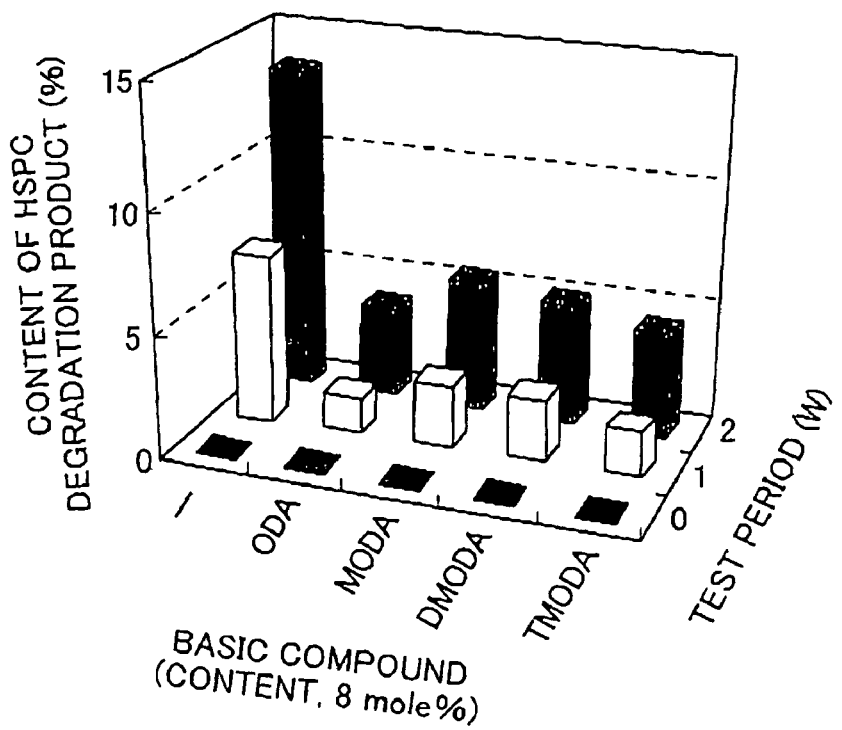
FIG. 4 is a view showing content (%) of the degradation product of HSPC in the storage test.
Figure 5:
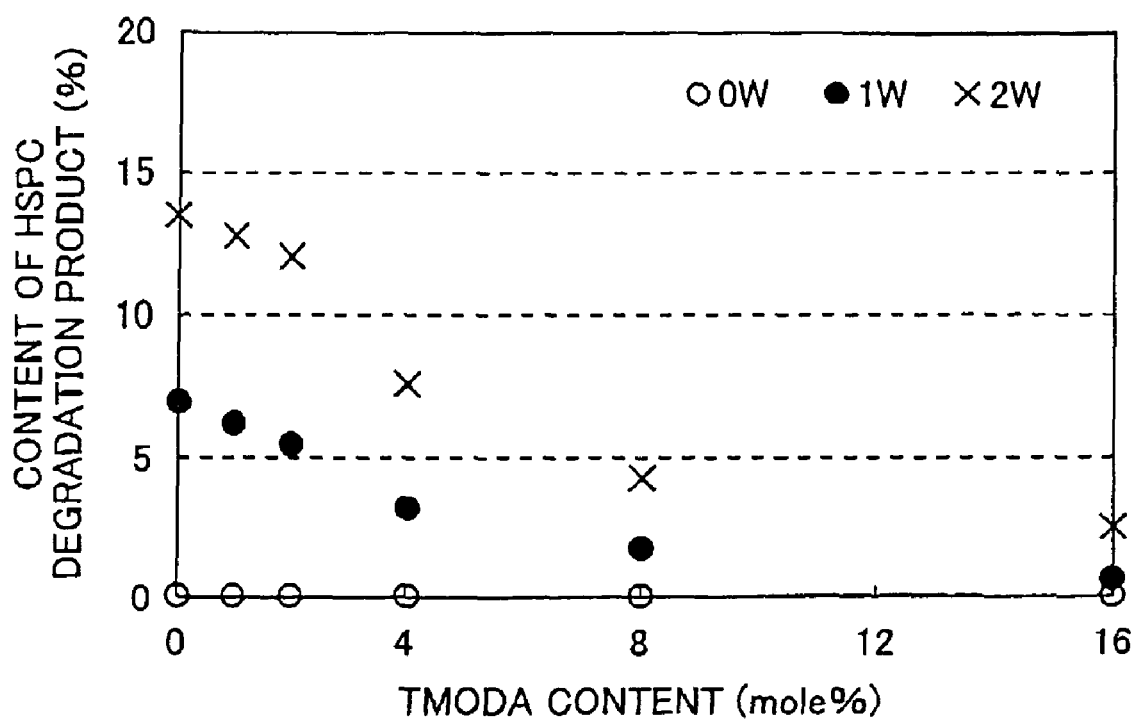
FIG. 5 is a view showing content (%) of the degradation product of HSPC in the storage test.

The results of the Test Example 4 are shown in FIGS. 4 and 5.

As shown in FIG. 4, the content (%) of the degradation product of the HSPC of the liposome preparation of Example 4 is lower than the liposome of the Example 1, indicating the suppression of the hydrolysis of the HSPC. It was also indicated that the content (%) of the degradation product of the HSPC was not largely dependent on the structure of the basic compound.

FIG. 5 shows content (%) of the degradation product of the HSPC in relation to the content (% by mole) of the basic compound (TMODA) at test periods of 0 week, 1 week, and 2 weeks (0 W, 1 W, and 2 W in FIG. 5) for the liposome preparations of the Example 4. As shown in FIG. 5, the content (%) of the degradation product of the HSPC was suppressed with the increase in the content (% by mole) of the basic compound.

As described above, degradation of the $PEG_{5000}$-DSPE can be prevented by loading the PEG lipid ($PEG_{5000}$-DSPE) on the exterior of the lipid bilayer as described above. In addition, the degradation of the $PEG_{5000}$-DSPE, and the hydrolysis of the HSPC can be further prevented by introducing a basic compound in the lipid layer, and the liposome preparation can be stabilized even if a drug which should be under an acidic condition is retained in the internal aqueous phase. The present invention has enabled to prevent instabilization of the lipid bilayer, leakage of the drug introduced in the liposome, aggregation of the liposome, decrease in the effect of preventing adsorption of the liposome to plasma protein or opsonin protein, loss of liposome stability in blood, and the like.

The invention claimed is:

1. A liposome preparation comprising a unilamellar vesicle comprising a lipid bilayer comprising a phospholipid as the main membrane component, the unilamellar vesicle further comprising an interior aqueous phase at a pH of up to 5, wherein the unilamellar vesicle comprises a drug loaded therein, and wherein the unilamellar vesicle is modified with a hydrophilic macromolecule only on its exterior surface and the hydrophilic macromolecule is introduced as a phospholipid derivative of the hydrophilic macromolecule.

2. The liposome preparation according to claim 1, wherein the drug is a drug that is unstable at a pH higher than 5.

3. The liposome preparation according to claim 1, wherein the drug loaded is at a concentration of 0.05 mole/mole lipid.

4. The liposome preparation according to claim 1, wherein the drug loaded is at a concentration of 0.1 mole/mole lipid.

5. The liposome preparation according to claim 1, wherein the main membrane component is a phospholipid having a phase transition temperature of at least 50° C.

6. The liposome preparation according to claim 1, wherein the phospholipid is a hydrogenated phospholipid.

7. The liposome preparation according to claim 1, wherein the phospholipid is a sphingophospholipid.

8. The liposome preparation according to claim 1, wherein the lipid bilayer comprises a lipid other than the phospholipid as a membrane component.

9. The liposome preparation according to claim 6, wherein the lipid bilayer further comprises a cholesterol as a component.

10. The liposome preparation according to claim 1, wherein the lipid bilayer further comprises a basic compound containing a group selected from amino group, amidino group, and guanidino group as a component.

11. The liposome preparation according to claim 10, wherein the basic compound is 3,5-dipentadecyloxybenzamidine hydrochloride.

12. The liposome preparation according to claim 1, wherein the hydrophilic macromolecule is polyethylene glycol having a molecular weight of 500 to 10,000 Dalton.

13. The liposome preparation according to claim 1, wherein the liposome preparation has an average size of 40 to 140 nm.

14. The liposome preparation according to claim 1, wherein the liposome preparation has an average size of 50 to 130 nm.

15. The liposome preparation according to claim 1, wherein the liposome preparation has an average size of 60 to 120 nm.

16. The liposome preparation according to claim 1, wherein the interior aqueous phase has a pH of 2 to 5.

17. A method for producing a liposome preparation of claim 1 comprising the steps of
preparing a vesicle having a unilamellar layer structure of a lipid bilayer containing a phospholipid so that the interior aqueous phase has a pH of up to 5;
adding a lipid derivation of the hydrophilic macromolecule to modify only the exterior surface of the vesicle; and
encapsulating the drug in the interior of the liposome either by preliminarily adding the drug to the interior aqueous phase in the course of the preparation of the vesicle, or alternatively, by adding the drug from the exterior of the vesicle after preparing the vesicle by penetration through the lipid bilayer.

* * * * *